United States Patent
Anderson et al.

(10) Patent No.: US 11,305,063 B2
(45) Date of Patent: Apr. 19, 2022

(54) MEDICAMENT DELIVERY DEVICE

(71) Applicant: Consort Medical PLC, Hemel Hempstead (GB)

(72) Inventors: Ian Anderson, Dullingham (GB); Alastair Willoughby, Cambridge (GB); Rachel Koppelman, Cambridge (GB)

(73) Assignee: Consort Medical PLC, Hemel Hempstead (GB)

( * ) Notice: Subject to any disclaimer, the term of this patent is extended or adjusted under 35 U.S.C. 154(b) by 146 days.

(21) Appl. No.: 16/482,363

(22) PCT Filed: Jan. 22, 2018

(86) PCT No.: PCT/GB2018/050182
§ 371 (c)(1),
(2) Date: Jul. 31, 2019

(87) PCT Pub. No.: WO2018/142106
PCT Pub. Date: Aug. 9, 2018

(65) Prior Publication Data
US 2020/0001010 A1    Jan. 2, 2020

(30) Foreign Application Priority Data
Feb. 6, 2017 (GB) ...................... 1701929

(51) Int. Cl.
*A61M 5/20* (2006.01)
*A61M 5/32* (2006.01)

(52) U.S. Cl.
CPC ........ *A61M 5/2046* (2013.01); *A61M 5/3232* (2013.01)

(58) Field of Classification Search
None
See application file for complete search history.

(56) References Cited

U.S. PATENT DOCUMENTS 5,383,851 A * 1/1995 McKinnon, Jr. ........ A61M 5/30
604/143
6,045,534 A    4/2000 Jacobsen et al.
(Continued)

FOREIGN PATENT DOCUMENTS

GB    2537638 A    10/2016
GB    2537639 A    10/2016
(Continued)

OTHER PUBLICATIONS

International Search Report and Written Opinion dated Apr. 5, 2018, for International Application No. PCT/GB2018/050182, International Filing Date Jan. 22, 2018, consisting of 10-pages.
(Continued)

*Primary Examiner* — Bhisma Mehta
*Assistant Examiner* — Robert F Allen
(74) *Attorney, Agent, or Firm* — Christopher & Weisberg, P.A.

(57) ABSTRACT

A medicament delivery device comprises a housing and a syringe axially movable in the housing and the syringe having a barrel. The device further comprises a stopper axially movable in the barrel and which separates a first chamber and second chamber from one another. The stopper is axially movable in the barrel in response to a vapour pressure being received in the second chamber. The device also includes a biasing mechanism to axially move the syringe in the housing between a first syringe position and a second syringe position in response to a first reduction in the vapour pressure in the second chamber. In the first syringe position venting of the propellant from the second chamber through a first fluid pathway is permitted to enable the first reduction in the vapour pressure in the second chamber while venting of the propellant from the second chamber through a second fluid pathway is substantially (Continued)

prevented. In the second syringe position venting of the propellant from the second chamber through the second fluid pathway is permitted to enable a second reduction in the vapour pressure in the second chamber.

20 Claims, 5 Drawing Sheets

(56) References Cited

U.S. PATENT DOCUMENTS

| | | | |
|---|---|---|---|
| 6,447,475 B1 | 9/2002 | Castellano | |
| 7,658,734 B2* | 2/2010 | Adair | A61M 5/16831 |
| | | | 604/523 |
| 2015/0151047 A1* | 6/2015 | Anderson | B65B 51/26 |
| | | | 604/148 |
| 2016/0213399 A1* | 7/2016 | Eckert | A61M 5/329 |
| 2016/0361496 A1* | 12/2016 | Guillermo | A61M 5/2033 |

FOREIGN PATENT DOCUMENTS

| | | |
|---|---|---|
| JP | 2005514082 A | 5/2005 |
| JP | 2015519964 A | 7/2015 |
| WO | 2016170346 A1 | 10/2016 |

OTHER PUBLICATIONS

Search Report dated Jun. 7, 2017, for Great Britain Application No. GB1701929.0, Filing Date Feb. 6, 2017, consisting of 3-pages.
Japanese Office Action dated Sep. 28, 2021, for corresponding Japanese Application No. 2019-542156; consisting of 7-pages.
Examination Report dated Sep. 17, 2021, for corresponding Indian Application No. 201937032973; consisting of 6-pages.

* cited by examiner

MEDICAMENT DELIVERY DEVICE

CROSS-REFERENCE TO RELATED APPLICATIONS

This application is a Submission under 35 U.S.C. § 371 for U.S. National Stage Patent Application of, and claims priority to, International Application Number PCT/GB2018/050182 entitled A MEDICAMENT DELIVERY DEVICE, filed Jan. 22, 2018, which is related to and claims priority to Great Britain Patent Number 1701929.0, filed Feb. 6, 2017, the entirety of all of which are incorporated herein by reference.

TECHNICAL FIELD

The invention relates to a medicament delivery device for delivering a dose of medicament to a patient.

BACKGROUND

Medical devices comprising automatically actuatable syringes, often referred to as autoinjectors, are known. These devices include a power source, for example a compressed spring or a container of pressurised gas, which is used to deliver a dose of medicament to a patient. Many such devices deliver the dose of medicament into an injection site through a needle and may be configured to automatically retract the needle at the end of delivery, removing the needle from the injection site and covering it to make safe the device. Such arrangements may reduce the risk of potential needle stick injuries and/or may reduce anxiety associated with needle phobia, as the needle is not visible after delivery.

It is an object of embodiments of the invention to at least mitigate one or more of the problems of the prior art.

SUMMARY OF THE INVENTION

According to an aspect of the invention, there is provided a medicament delivery device comprising: a housing; a syringe axially movable in the housing, the syringe having a barrel; a stopper axially movable in the barrel, the stopper separating a first chamber and a second chamber from one another, the first chamber being axially forward of the stopper and configured to receive a medicament and the second chamber being axially rearward of the stopper and configured to receive a propellant from a propellant source to provide a vapour pressure to the second chamber, the stopper being axially movable in the barrel between a first stopper position and a second stopper position in response to the vapour pressure being received in the second chamber; and a biasing mechanism configured to axially move the syringe in the housing between a first syringe position and a second syringe position in response to a first reduction in the vapour pressure in the second chamber, wherein in the first syringe position venting of the propellant from the second chamber through a first fluid pathway is permitted to enable the first reduction in the vapour pressure in the second chamber while venting of the propellant from the second chamber through a second fluid pathway is substantially prevented, and wherein in the second syringe position venting of the propellant from the second chamber through the second fluid pathway is permitted to enable a second reduction in the vapour pressure in the second chamber. This arrangement may allow for improved retraction of a needle of the device. The first and second fluid pathways may be configured to enable a faster flow rate of propellant out of the second chamber when venting the propellant from the second chamber through the second fluid pathway than when venting the propellant from the second chamber through the first fluid pathway.

Optionally, in the first stopper position venting of the propellant from the second chamber through the first fluid pathway may be substantially prevented and in the second stopper position venting of the propellant from the second chamber through the first fluid pathway may be permitted to enable the first reduction in the vapour pressure in the second chamber.

In certain embodiments, the biasing mechanism may be configured to axially move the syringe between the second syringe position and a third syringe position in response to the second reduction in the vapour pressure in the second chamber.

The device may further comprise an expandable drive mechanism configured to receive the propellant from the propellant source to provide a vapour pressure to the drive mechanism, the drive mechanism being expandable in response to receiving the vapour pressure in the expandable drive mechanism to cause forward axial movement of the syringe in the housing. The syringe may be axially moveable between the third syringe position and the first syringe position in response to the vapour pressure being received in the expandable drive mechanism.

In certain embodiments, the expandable drive mechanism may comprise a first part fluidly sealable to the propellant source and a second part fluidly sealable to the barrel of the syringe, the second part being slidably and sealably engaged with the first part so as to be capable of expanding the drive housing in response to the vapour pressure being received in the drive housing. Additionally or alternatively, the expandable drive mechanism may at least partially define a third chamber configured to receive the propellant from the propellant source and the second chamber is configured to receive the propellant from the propellant source through the third chamber.

Optionally, the biasing mechanism may be compressible in response to the syringe being moved axially forward relative to the housing, e.g. from the third syringe position to the first and/or second syringe position, so as to provide at least in part a biasing force for biasing the syringe between the first syringe position and the second syringe position. Additionally or alternatively, the biasing mechanism may be compressible in response to the syringe being moved axially forward relative to the housing so as to provide at least in part a biasing force for biasing the syringe between the second syringe position and the third syringe position. The biasing mechanism may be a spring.

In certain embodiments, the stopper may be configured to selectively separate an opening of the first fluid pathway and the second chamber from one another to selectively prevent venting of the propellant from the second chamber through the first fluid pathway. Additionally or alternatively, the device may comprise a sealing surface configured to selectively seal an opening of the second fluid pathway to selectively prevent venting of the propellant from the second chamber through the second fluid pathway. The sealing surface may seal the opening of the second fluid pathway in response to the vapour pressure received in the drive mechanism. The sealing surface may seal the opening of the second fluid pathway in response to axially forward movement of the syringe. In certain embodiments, the sealing surface may comprise a resilient material. The housing may comprise the sealing surface.

Optionally, the device comprises the propellant source. The propellant source may comprise a volume of a liquefied gas propellant. The propellant source may comprise a propellant which includes a hydrofluoroalkane ("HFA"). Additionally or alternatively, the propellant source may comprise a propellant which includes a hydrofluoroolefin ("HFO")

BRIEF DESCRIPTION OF THE DRAWINGS

Embodiments of the invention will now be described by way of example only, with reference to the accompanying figures, in which.

DETAILED DESCRIPTION

FIGS. 1 to 5 show a medicament delivery device 10 according to an embodiment of the invention. The device 10 has particular application as an autoinjector device. As used herein, the terms "proximal" and "distal" denote directions and ends of the device 10 and components thereof. The term "proximal" refers to the direction toward an injection site during use of the device 10 to deliver a dose of medicament to a patient. Conversely, the term "distal" refers to the direction away from the injection site during use of the device 10 to deliver the dose of medicament to the patient. References herein to axial movements are to movements in the proximal direction and/or the distal direction. Specifically, references to forward axial movements are to movements towards a proximal end of the device 10 and references to rearward axial movements are to movements towards a distal end of the device 10.

The device 10 comprises a housing 12 and a syringe 14, the syringe 14 being axially moveable within the housing 12. The housing 12 may be a sleeve-like member configured to at least partially retain the syringe 14 therein. The syringe 14 comprises a barrel 16 having an open proximal end 16A. The open end 16A may have a needle 28 attached thereto. The device 10 has a first chamber 18 and a second chamber 20 (the second chamber 20 is visible in FIGS. 2 to 5). The device 10 further comprises a stopper 22 which is axially movable within the barrel 16 and separates the first chamber 18 and the second chamber 20 from one another. The first chamber 18 is axially forward of the stopper 22. The second chamber 20 is axially rearward of the stopper 22. The first chamber 18 is in the barrel 16 of the syringe 14 and is configured to receive the dose of medicament. The second chamber 20 is configured to receive a propellant from a propellant source 30. The needle 28 is in fluid communication with the first chamber 18 via the open end 16A of the barrel 16.

The device 10 further comprises a biasing mechanism 32. The biasing mechanism 32 is configured to provide a biasing force for axially moving the syringe 14 within the housing 12. In the illustrated embodiment, the biasing mechanism 32 comprises a compression spring 34 for biasing the syringe 14 axially rearwardly, i.e. in the distal direction, within the housing 12. It will be understood that in certain embodiments, the biasing mechanism 32 may comprise alternative means for moving the syringe 14 within the housing 12, e.g. the biasing mechanism 32 may comprise a resilient flexible member or a leaf spring.

The device 10 may further comprise an expandable drive mechanism 40 for axially moving the syringe 14 within the housing 12. In the embodiment shown in the accompanying figures, the expandable drive mechanism 40 includes a first part 42 and a second part 44. The second part 44 is slidably engaged within the first part 42. A first sliding seal 46 seals the first part 42 to the second part 44. The first sliding seal 46 permits axial movement of the second part 44 relative to the first part 42 and maintains a substantially fluid tight seal therebetween. In the illustrated embodiment, the first sliding seal 46 is fixed relative to first part 42, e.g. by attachment to the first part 42, and seals against the second part 44. However, embodiments are contemplated where the first sliding seal 46 is fixed relative to the second part 44, e.g. by attachment to the second part 44, and seals against the first part 42. Together, the first part 42 and the second part 44 define a third chamber 50 (the third chamber 50 is visible in FIGS. 2 to 4) of the device 10, at least in part. As shown in the accompanying figures, a distal end of the second part 44 may separate the second chamber 20 and the third chamber 50 from one another. The third chamber 50 may be configured to receive the propellant from the propellant source 30.

In the illustrated embodiment, the stopper 22 is slidably engaged with the second part 44. The stopper 22 may be a multi-component part, e.g. the stopper 22 may comprise a plunger seal, i.e. a bung, 22a coupled to a plunger rod 22b. The plunger seal 22a may be configured to seal against the barrel 16 to seal the stopper 22 to the barrel 16. A second sliding seal 48 seals the stopper 22 to the second part 44. The second sliding seal 48 permits axial movement of the stopper 22 relative to the second part 44 and maintains a substantially fluid tight seal therebetween. In the illustrated embodiment, the second sliding seal 48 is fixed relative to stopper 22, e.g. by attachment to the stopper 22, and seals against the second part 44. Together, the stopper 22 and the second part 44 define the second chamber 20, at least in part. In certain embodiments, the barrel 16 may also define the second chamber 20, in combination with the stopper 22 and the second part 44. In the embodiment shown in the figures, the first part 42 has a first fluid channel 42A fluidly connecting the propellant source 30 and the third chamber 50 to one another. Further, in the illustrated embodiment, the second part 44 has a second fluid channel 44A fluidly connecting the second chamber 20 and the third chamber 50 to one another. The second part 44 may abut a portion, e.g. a flange 52, of the barrel 16, such that the forward axial movement of the second part 44 relative to the housing 12 causes forward axial movement of the syringe 14 relative to the housing 12.

The device 10 further includes a first fluid pathway 60 (the first fluid pathway 60 is visible in FIGS. 3 and 4) for selectively venting the propellant from the second chamber 20. For example, the first fluid pathway 60 selectively fluidly connects the second chamber 20 to atmosphere. In the illustrated embodiment, the first fluid pathway 60 comprises a first opening 64 (the first opening 64 is visible in FIGS. 3 and 4). The first opening 64 may be formed in a side wall of the second part 44. In the illustrated embodiment, the stopper 22 separates the second chamber 20 and the first opening 64 from one another to prevent venting of the propellant from the second chamber 20 through the first fluid pathway 60, so long as the second sliding seal 48 is axially rearward of the first opening 64 within the second part 44. Movement of the second sliding seal 48 axially forward of the first opening 64 fluidly connects the second chamber 20 to atmosphere, i.e. the stopper 22 no longer separates the second chamber 20 and the first opening 64 from one another.

The device 10 also includes a second fluid pathway 62 for selectively venting the propellant from the second chamber 20. For example, the second fluid pathway 62 selectively fluidly connects the second chamber 20 to atmosphere, though independently of the first fluid pathway 60. As shown in the accompanying figures, the second fluid pathway 62 may comprise a pair of second openings 66 formed diametrically opposite one another in the second part 44. Each of the second openings 66 may be fluidly connected to a respective outlet channel 70 formed in the side wall of the second part 44. Of course, it will be understood that in certain embodiments the device 10 may comprise an alternative number of the second openings 66, e.g. one, three or four. The second openings 66 may be configured to face the proximal end of the device 10, i.e. each of the second opening 66 may span in a direction perpendicular to the direction of the axial movement of the syringe 14 within the housing 12. In the illustrated embodiment, each of the second openings 66 are sealable by a respective sealing surface 68 to prevent venting of the propellant from the second chamber 20 through the second fluid pathway 62. The sealing surfaces 68 may comprise a resilient material, e.g. rubber, to facilitate the effectiveness of the sealing surface 68 in preventing of the propellant from the second chamber 20 through the second fluid pathway 62. As shown in the accompanying figures, the housing 12 comprises the sealing surfaces 68.

The first and second fluid pathways 60, 62 may be configured to enable a faster flow rate of propellant when venting the propellant from the second chamber 20 through the second fluid pathway 62 than when venting the propellant from the second chamber 20 through the first fluid pathway 60. To this end, the first opening 64 may have a diameter of a lesser size than that of at least one of the second opening 66.

The propellant source 30 may be any suitable propellant for providing the vapour pressure to the second and/or third chambers 20, 50. In certain embodiments, the propellant may be a liquefied gas that vaporizes to provide a vapour pressure. In certain embodiments, the propellant may be or contain a hydrofluoroalkane ("HFA"), for example HFA 341a, HFA227, HFA 422D, HFA 507, or HFA 410A. In certain embodiments, the propellant may be or contain a hydrofluoroolefin ("HFO"), such as HFO 1234yf or HFO 1234ze.

Figure 1:
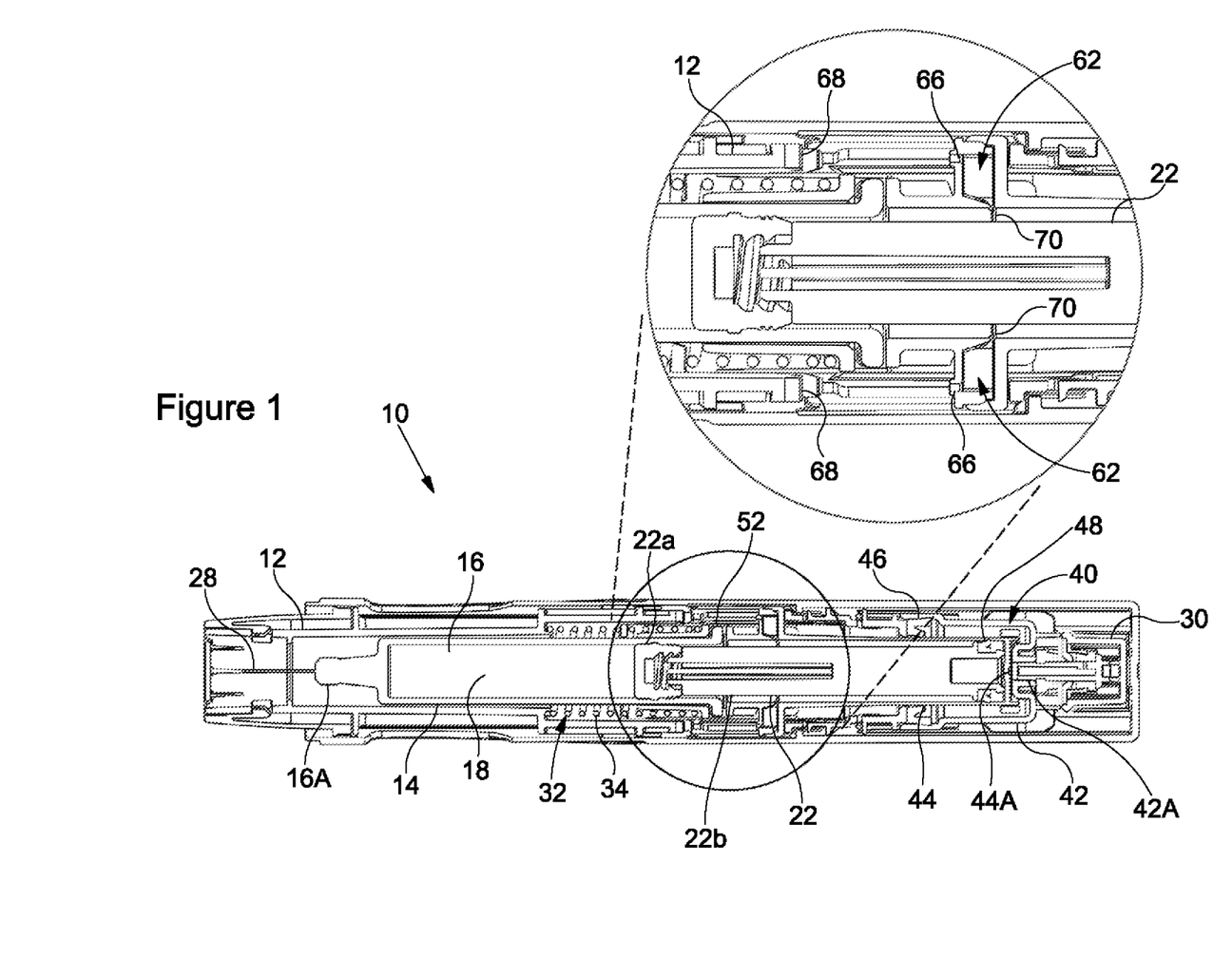
FIG. 1 shows a cross-sectional view of a medicament delivery device according to an embodiment of the invention prior to actuation the device.

FIG. 1 shows the syringe 14 in a distal syringe position ("a third syringe position") and the stopper 20 in a first stopper position. With the syringe 14 in the distal position, the needle 28 is in a covered and/or a retracted position, i.e. the needle is within the housing 12. This arrangement may minimise the risk of needle stick injuries when using the device 10 and/or may reduce anxiety associated with needle phobia, as the needle 28 is not visible to the patient prior to use. Further, with the syringe 14 in the distal position, the second openings 66 are unsealed. With the stopper 22 in the first stopper position, the first the stopper 22 fluidly separates the second chamber 20 and the first opening 64 from one another, as the second slidable seal 48 is axially rearward of the first opening 64. Additionally, the stopper 22 may fluidly separate the first opening 64 and the second openings 66 from one another. In certain embodiments, the stopper 22 fluidly separates the second chamber 20 and the second openings 66 from one another, as the second slidable seal 48 is axially rearward of the first openings 66. FIG. 1 shows the device 10 in a configuration prior to actuation.

Figure 2:
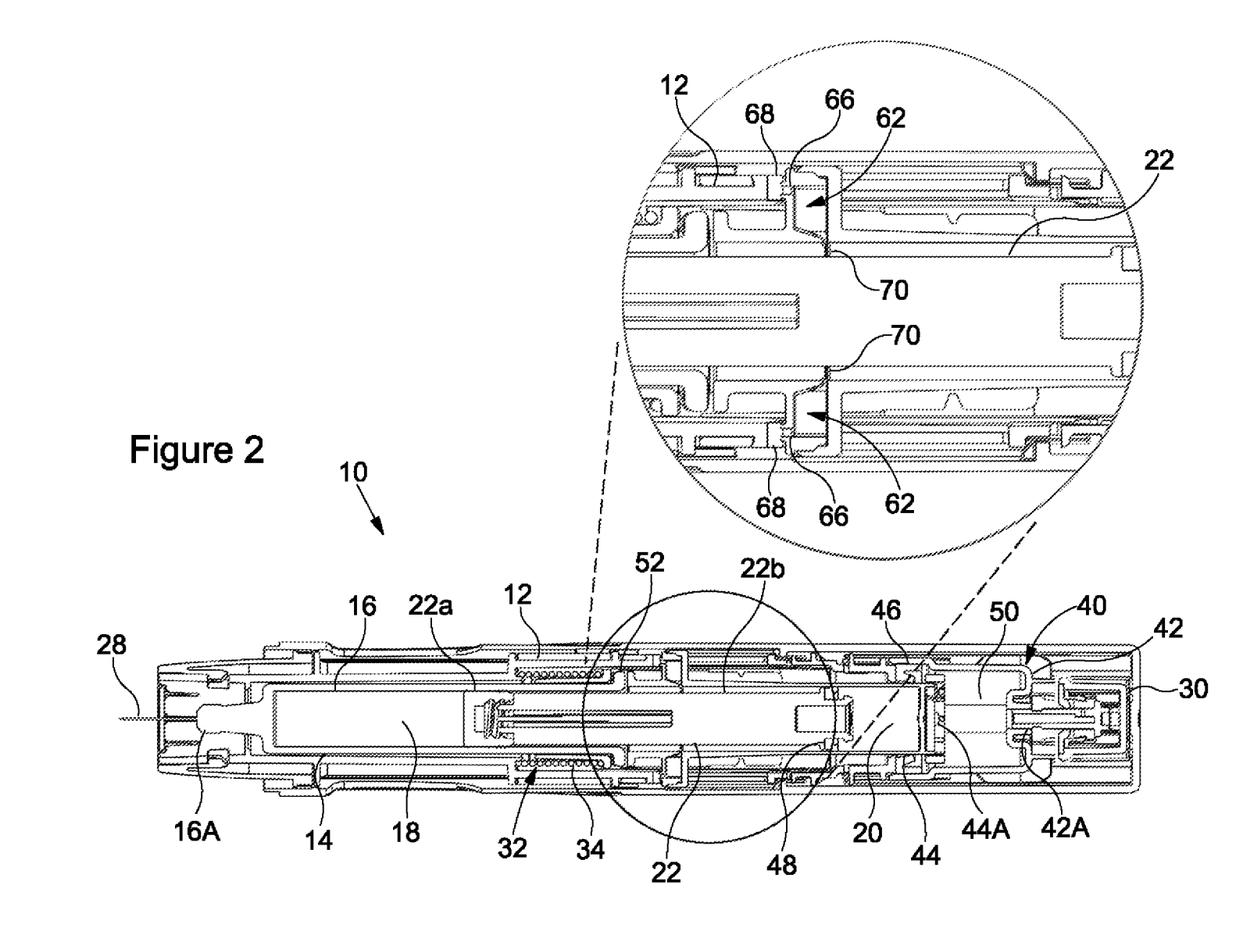
FIG. 2 shows a cross-sectional view of the device of FIG. 1 post actuation and having a needle extending from an end of the device.

FIG. 2 shows the syringe 14 in a proximal syringe position ("a first syringe position"), the syringe 14 having moved axially forward, i.e. in a proximal direction, within the housing 12 from the distal syringe position shown in FIG. 1. The axially forward movement of the syringe 14 causes the needle 28 to extend from the proximal end of the device 10 such that the needle 28 may penetrate the injection site of the patient. Forward axial movement of the syringe 14 is initiated by actuation of the propellant source 30. Upon actuation of the device 10, propellant may be dispensed from the propellant source 30 to enter the third chamber 50 to provide a vapour pressure thereto. Propellant flows from the propellant source 30 to the third chamber 50 through the first fluid channel 42A. In the embodiment shown in the accompanying figures, the second part 44 moves axially forward relative to the first part 42 in response to the vapour pressure received in the third chamber 50 being sufficient to overcome the biasing force of the biasing mechanism 32, in addition to any frictional forces between the first part 42 and the second part 44. It will be understood that the vapour pressure received in the 15 third chamber 50 acts on the distal end of the second part 44. As the second part 44 moves axially forward relative to the first part 42, the volume of the third chamber 50 is increased. Thus, the drive mechanism 40 expands in response to receiving the vapour pressure therein to cause forward axial movement of the syringe 14 within the housing 12. The syringe 14 is moved axially forward from the distal syringe position to the proximal syringe position due to abutment of the second part 44 and the barrel 16 of the syringe 14. The syringe 14 may move axially forward so as cause the needle 28 to penetrate the injection site, e.g. for sub-cutaneous delivery of the medicament, the needle 28 may penetrate the injection site to a tissue depth of approximately 6 mm. In certain embodiments, the syringe 14 may move axially forward such that the needle 28 penetrates the injection site to an alternative tissue depth, e.g. for intra-muscular delivery, the needle 28 may penetrate the injection site to a tissue of depth of at least 10 mm. In the illustrated embodiment, forward movement of the syringe 14 within the housing 12 from the distal syringe position to the proximal syringe position compresses the biasing mechanism 32 so as to increase the biasing force for biasing the syringe 14 axially rearwardly within the housing 12. Further, with the syringe 14 in the proximal syringe position, venting of the propellant from the second chamber 20 through a second fluid pathway 62 is substantially prevented. In the illustrated embodiment, the axially forward movement of the second part 44 moves the second openings 66 axially forward to abut the respective sealing surfaces 68 of the housing 12. This action substantially seals the second openings 66. The second openings 66 are held against the respective sealing surfaces 68 of the housing 12 in response to the vapour pressure received in the drive mechanism 40. With reference to the illustrated embodiment, the second openings 66 are held against the respective sealing surfaces 68 of the housing 12 in response to the vapour pressure received in the third chamber 50, the third chamber 50 forming part of the drive mechanism 40. Thus, the vapour pressure in the drive mechanism 40 may facilitate the effectiveness of the sealing surfaces 68 in preventing of the propellant from the second chamber 20 through the second fluid pathway 62.

In the illustrated embodiment, as propellant enters the third chamber 50, it begins to flow through the second fluid channel 44A and enter the second chamber 20. The second chamber 20 may pressurise at a different rate to the third chamber 50, as a flow restriction may be provided by the second flow channel 44A. The stopper 22 moves axially forward relative to the second part 42 in response to the vapour pressure received in the second chamber 50 being sufficient to overcome a fluid resistance provided by the medicament in the first chamber 18, in addition to any frictional forces between the stopper 22 and the barrel 16 and/or between the stopper 22 and the second part 44. It will be understood that the vapour pressure received in the second chamber 20 acts on the stopper 22. Medicament may be expelled from the first chamber 18 through the open proximal end 16A of the barrel 16 in response to forward movement of the stopper 22 within the barrel 16 of the syringe 14, e.g. as the stopper 22 moves from the first stopper position to the second stopper position.

Figure 3:
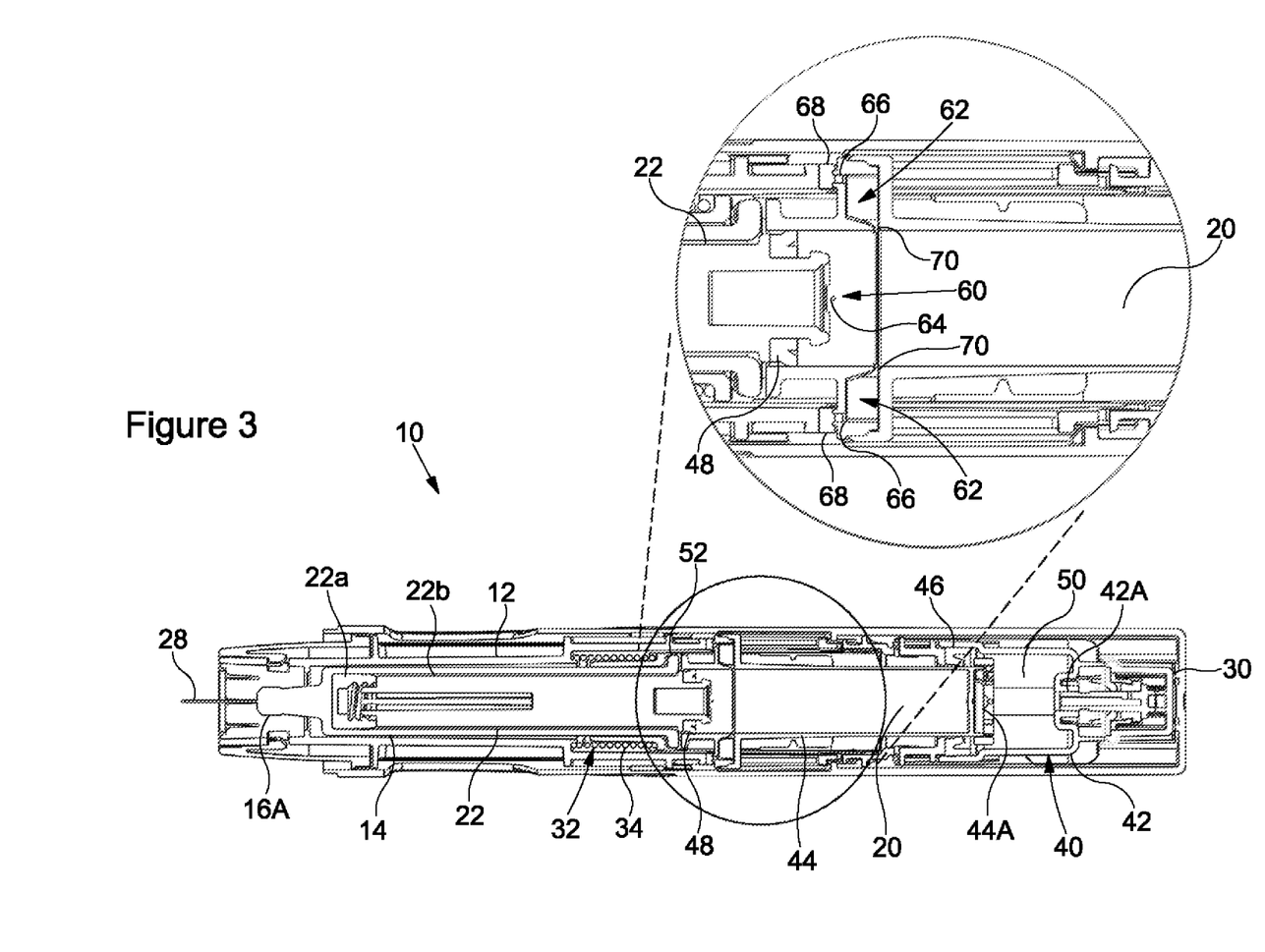
FIG. 3 shows a further cross-sectional view of the device of FIG. 1 at the end of delivery of a medicament.

FIG. 3 shows the syringe 14 in the proximal syringe position and the stopper 22 in the second stopper position, the stopper 22 having moved axially forward to a maximum extent within the barrel 16 in response to the vapour pressure in the second chamber 20. With the stopper 22 in the second stopper position, substantially all of the dose of the medicament has been expelled from the first chamber 18. Thus, the volume of the first chamber 18 may be reduced to substantially zero. Further, with the stopper 22 in the second stopper position, the second sliding seal 48 is axially forward of the first opening 64, fluidly connecting the second chamber 20 to atmosphere. Thus, venting of the propellant from the second chamber 20 through the first fluid pathway 60 is permitted to enable a first reduction in the vapour pressure in the second chamber 20. Vapour pressure received in the third chamber 50 remains sufficient to hold the syringe 14 in the proximal syringe position.

Figure 4:
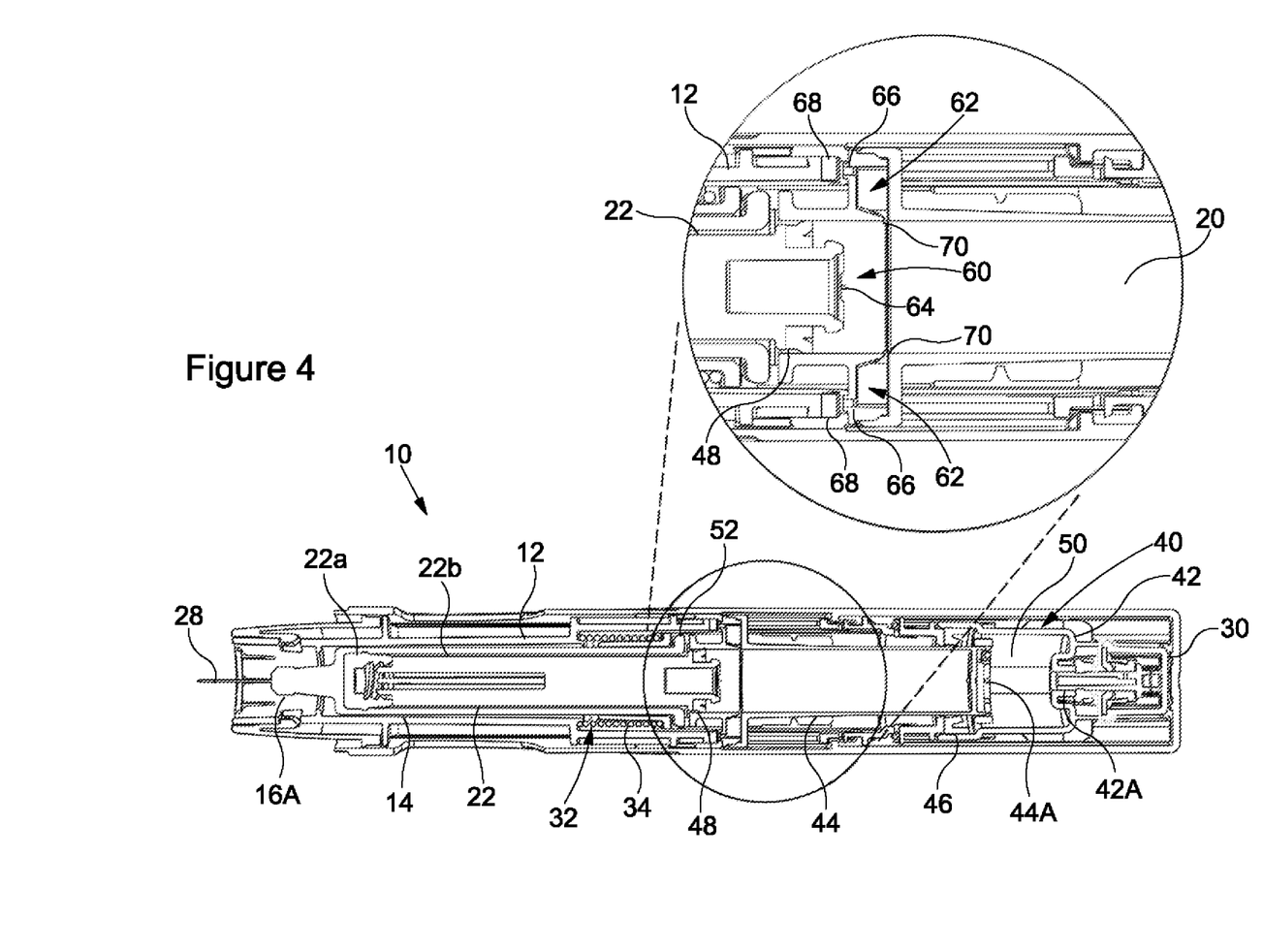
FIG. 4 shows a further cross-sectional view of the device of FIG. 1 immediately after beginning retraction of the needle.

FIG. 4 shows the syringe 14 in an intermediate syringe position ("a second syringe position"), i.e. a position intermediate the distal syringe position and the proximal syringe position, the syringe 14 having moved axially rearwardly within the housing 12 from the proximal syringe position shown in FIGS. 2 and 3. Rearward axial movement of the syringe 14 is initiated upon the first reduction in the vapour pressure received in the second chamber 20. In the embodiment shown in the accompanying figures, the syringe 14 moves axially rearwardly relative to the housing 12 in response to the first reduction in the vapour pressure received in the second chamber 20 causing a reduction in the vapour pressure received in the third chamber 50. As the vapour pressure received in the third chamber 50 reduces, it is eventually no longer sufficient to overcome the biasing force of the biasing mechanism 32, in addition to any frictional forces between the stopper 22 and the second part 44. Consequently, the biasing mechanism 32 moves the syringe 14 within the housing 12 between the proximal syringe position and the intermediate syringe position in response to the first reduction in the vapour pressure in the second chamber 20. This axially rearward movement of the syringe 14 within the housing 12 beings to retract the needle 28 from the injection site.

Further, the second part 44 is moved axially rearwardly within the housing 12 due to abutment of the second part 44 and the barrel 16 of the syringe 14. The axially rearward movement the second part 44 moves the second openings 66 axially rearward away from the respective sealing surfaces 68 of the housing 12. This action unseals the second openings 66, providing an additional fluid connection between the second chamber 20 and atmosphere. Propellant flows from the second chamber 20 through the outlet channels 70 to the second openings 66. Thus, in the second syringe position venting of the propellant from the second chamber 20 through the second fluid pathway 62 is permitted to enable a second reduction in the vapour pressure in the second chamber 20. The second reduction in vapour pressure may be a faster reduction in the vapour pressure than the first reduction in the vapour pressure.

Figure 5:
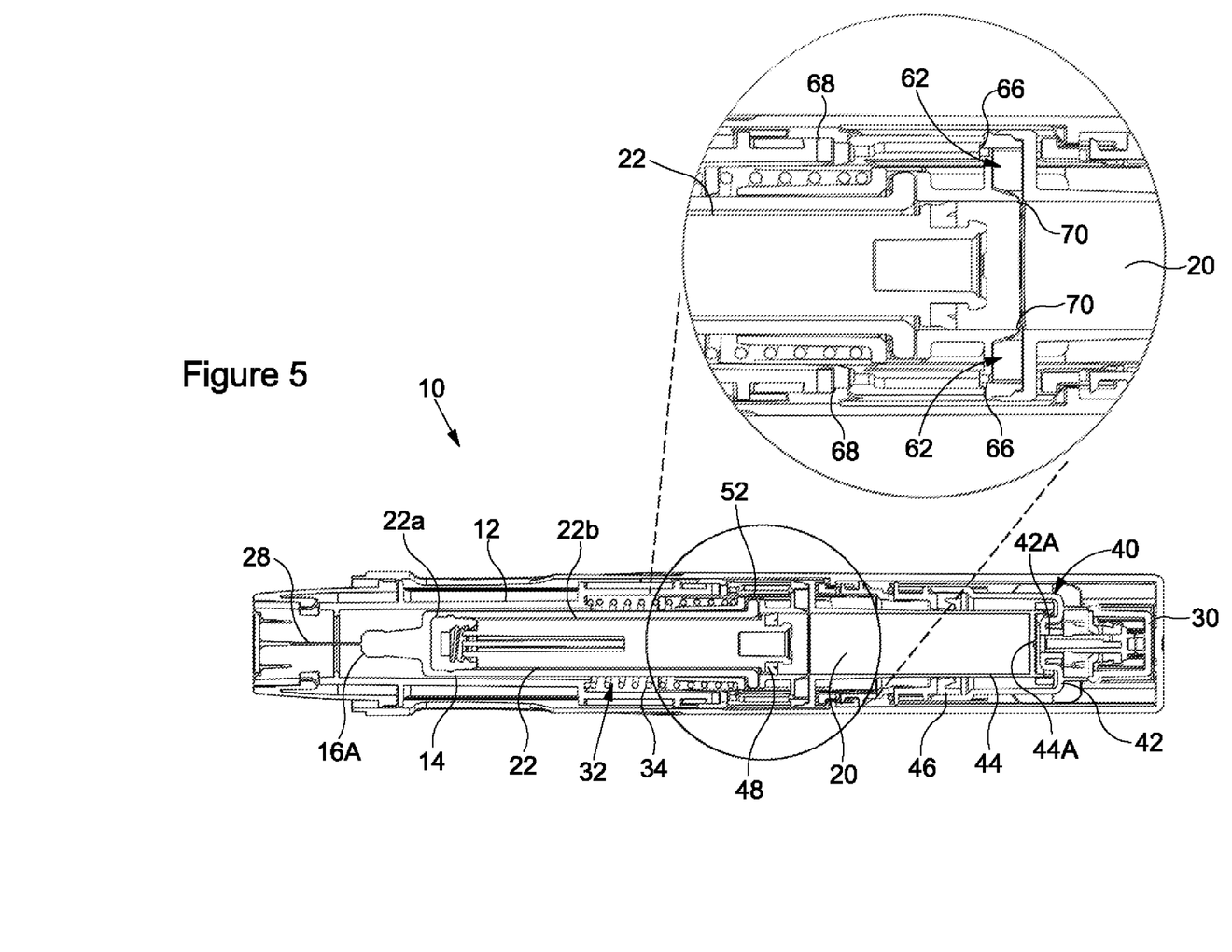
FIG. 5 shows a further cross-sectional view of the device of FIG. 1 post retraction of the needle.

FIG. 5 shows the syringe 14 in the distal syringe position, the syringe 14 having moved axially rearwardly to a maximum extent within the housing 12 from the intermediate syringe position shown in FIG. 4. This continued rearward axial movement of the syringe 14 occurs in response to the second reduction in the vapour pressure received in the second chamber 20. In the embodiment shown in the accompanying figures, the syringe 14 continues to move axially rearwardly relative to the housing 12 as the second reduction in the vapour pressure received in the second chamber 20 causes a further reduction in the vapour pressure received in the third chamber 50. The biasing mechanism 32 moves the syringe 14 within the housing 12 between the intermediate syringe position and the distal syringe position in response to second reduction in the vapour pressure in the second chamber 20. This axially rearward movement of the syringe 14 between the intermediate syringe position and the distal syringe position may be a faster movement than the axially rearward movement of the syringe 14 between proximal syringe position and the intermediate syringe position. As described above, with the syringe 14 in the distal position, the needle 28 is in a covered and/or a retracted position, i.e. the syringe 14 is fully retracted from the injection site.

The venting the second chamber 20 through the first fluid pathway 60 may allow for sufficient vapour pressure to be maintained in the second chamber 20 to deliver a complete dose, or at least a near complete dose, of the medicament, before venting of the second chamber 20 through the second fluid pathway effects rapid retraction of the needle 28.

The invention is not restricted to the details of any foregoing embodiments, e.g. embodiments are contemplated without the third chamber 50. In certain embodiments, the distal end of the second part may be a substantially open end. Thus, the second chamber 20 may be defined by the stopper 22, the first part 42 and the second part 44, at least in part. In such embodiments, the second part 44 may move axially forward relative to the first part 42 in response to the vapour pressure being received in the second chamber 20. Further, in certain embodiments, the barrel 16 may not include the needle 28. Indeed, in certain embodiments, a nozzle or an applicator may be affixed or may be coupled to the open end 16A of the barrel 16.

In the illustrated embodiment, the syringe 14 is shown in the distal syringe position prior to actuation of the device 10. However, the syringe 14 may be in an alternative syringe position ("a fourth syringe position") prior to actuation, i.e. a syringe position axially forward or axially rearward of the distal position. Also, the first opening 64 could be axially rearward of the second sliding seal 48 when the stopper 22 is in the first position, to allow for venting of the second chamber 20 upon actuation of the device 10.

All of the features disclosed in this specification (including any accompanying claims and drawings) may be combined in any combination, except combinations where at least some of such features and/or steps are mutually exclusive. Each feature disclosed in this specification (including any accompanying claims and drawings), may be replaced by alternative features serving the same, equivalent or similar purpose, unless expressly stated otherwise. Thus, unless expressly stated otherwise, each feature disclosed is one example only of a generic series of equivalent or similar features.

The invention extends to any novel one, or any novel combination, of the features disclosed in this specification (including any accompanying claims and drawings). The claims should not be construed to cover merely the foregoing embodiments, but also any embodiments which fall within the scope of the claims.

As used herein, the terms "include" and "comprise" are used synonymously, which terms and variants thereof are to be construed as non-limiting.

The invention claimed is:

1. A medicament delivery device comprising:
   a housing;
   a syringe axially movable in the housing, the syringe having a barrel;
   a stopper axially movable in the barrel, the stopper separating a first chamber and a second chamber from one another, the first chamber being axially forward of the stopper and configured to receive a medicament and the second chamber being axially rearward of the stopper and configured to receive a propellant from a propellant source to provide a vapour pressure to the second chamber, the stopper being axially movable in the barrel between a first stopper position and a second stopper position in response to the vapour pressure being received in the second chamber; and
   a biasing mechanism configured to axially move the syringe in the housing between a first syringe position and a second syringe position in response to a first reduction in the vapour pressure in the second chamber,
   wherein when the syringe is in the first syringe position, venting of the propellant from the second chamber through a first fluid pathway is permitted to enable the first reduction in the vapour pressure in the second chamber while venting of the propellant from the second chamber through a second fluid pathway is substantially prevented, and
   wherein when the syringe is in the second syringe position venting of the propellant from the second chamber through the second fluid pathway is permitted to enable a second reduction in the vapour pressure in the second chamber.

2. The medicament delivery device of claim 1, wherein the first and second fluid pathways are configured to enable a faster flow rate of propellant out of the second chamber when venting the propellant from the second chamber through the second fluid pathway than when venting the propellant from the second chamber through the first fluid pathway.

3. The medicament delivery device of claim 1, wherein when the stopper is in the first stopper position venting of the propellant from the second chamber through the first fluid pathway is substantially prevented and when the stopper is in the second stopper position, venting of the propellant from the second chamber through the first fluid pathway is permitted to enable the first reduction in the vapour pressure in the second chamber.

4. The medicament delivery device of claim 1, wherein the biasing mechanism is configured to axially move the syringe between the second syringe position and a third syringe position in response to the second reduction in the vapour pressure in the second chamber.

5. The medicament delivery device of claim 1, wherein the medicament delivery device further comprises an expandable drive mechanism configured to receive the propellant from the propellant source to provide a vapour pressure to the expandable drive mechanism, the expandable drive mechanism being expandable in response to receiving the vapour pressure in the expandable drive mechanism to cause forward axial movement of the syringe in the housing.

6. The medicament delivery device of claim 5, wherein the biasing mechanism is configured to axially move the syringe between the second syringe position and a third syringe position in response to the second reduction in the vapour pressure in the second chamber and wherein the syringe is axially moveable between the third syringe position and the first syringe position in response to the vapour pressure being received in the expandable drive mechanism.

7. The medicament delivery device of claim 5, wherein the expandable drive mechanism comprises a first part fluidly sealable to the propellant source and a second part fluidly sealable to the barrel of the syringe, the second part being slidably and sealably engaged with the first part so as to be capable of expanding the expandable drive mechanism in response to the vapour pressure being received in the expandable drive mechanism.

8. The medicament delivery device of claim 5, wherein the expandable drive mechanism at least partially defines a third chamber configured to receive the propellant from the propellant source and the second chamber is configured to receive the propellant from the propellant source through the third chamber.

9. The medicament delivery device of claim 5, wherein the biasing mechanism is configured to axially move the syringe between the second syringe position and a third syringe position in response to the second reduction in the vapour pressure in the second chamber; and
   where the biasing mechanism is compressible in response to the syringe being moved axially forward relative to the housing so as to provide at least in part a biasing force for biasing the syringe between the second syringe position and the third syringe position.

10. The medicament delivery device of claim 1, wherein the biasing mechanism is compressible in response to the syringe being moved axially forward relative to the housing so as to provide at least in part a biasing force for biasing the syringe between the first syringe position and the second syringe position.

11. The medicament delivery device of claim 1, wherein the biasing mechanism comprises a spring.

12. The medicament delivery device of claim 1, wherein the stopper is configured to selectively separate an opening of the first fluid pathway and the second chamber from one another to selectively prevent venting of the propellant from the second chamber through the first fluid pathway.

13. The medicament delivery device of claim 1, wherein the medicament delivery device further comprises a sealing surface configured to selectively seal an opening of the second fluid pathway to selectively prevent venting of the propellant from the second chamber through the second fluid pathway.

14. The medicament delivery device of claim 13, wherein the sealing surface seals the opening of the second fluid pathway in response to the vapour pressure in an expandable drive mechanism, the expandable drive mechanism being configured to receive the propellant from the propellant source to provide a vapour pressure to the expandable drive mechanism, the expandable drive mechanism being expandable in response to receiving the vapour pressure in the expandable drive mechanism to cause forward axial movement of the syringe in the housing.

15. The medicament delivery device of claim 13, wherein the sealing surface seals the opening of the second fluid pathway in response to axially forward movement of the syringe.

16. The medicament delivery device of claim 13, wherein the sealing surface comprises a resilient material.

17. The medicament delivery device of claim 13, wherein the housing comprises the sealing surface.

18. The medicament delivery device of claim 1, wherein the medicament delivery device further comprises the propellant source.

19. The medicament delivery device of claim 1, wherein the propellant source comprises a volume of a liquefied gas propellant.

20. The medicament delivery device of claim 1, wherein the propellant source comprises a propellant which includes at least one of the group consisting of a hydrofluoroalkane ("HFA") and a hydrofluoroolefin ("HFO").

* * * * *